United States Patent
Hvichia

(10) Patent No.: US 9,939,425 B2
(45) Date of Patent: *Apr. 10, 2018

(54) METHODS FOR SEGREGATING PARTICLES USING AN APPARATUS WITH A SIZE-DISCRIMINATING SEPARATION ELEMENT HAVING AN ELONGATE LEADING EDGE

(71) Applicant: ANGLE North America, Inc., Philadelphia, PA (US)

(72) Inventor: Georgi Hvichia, Philadelphia, PA (US)

(73) Assignee: ANGLE North America, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/790,981

(22) Filed: Oct. 23, 2017

(65) Prior Publication Data

US 2018/0045708 A1    Feb. 15, 2018

Related U.S. Application Data

(63) Continuation of application No. 15/434,249, filed on Feb. 16, 2017, now Pat. No. 9,851,344, which is a (Continued)

(51) Int. Cl.
  *G01N 33/49*     (2006.01)
  *C12N 5/09*      (2010.01)
  *B01L 3/00*      (2006.01)

(52) U.S. Cl.
  CPC ...... *G01N 33/491* (2013.01); *B01L 3/502753* (2013.01); *C12N 5/0694* (2013.01); (Continued)

(58) Field of Classification Search
  CPC ............... G01N 33/491; G01N 33/574; G01N 33/4915; G01N 15/0272; (Continued)

(56) References Cited

U.S. PATENT DOCUMENTS 7,651,838 B2 *  1/2010  Paterlini-Brechot  C12Q 1/6879
                                             435/6.11
7,846,743 B2   12/2010  Tai et al.
(Continued)

FOREIGN PATENT DOCUMENTS

WO      03/008931 A2    1/2003
WO    2005/036139 A1    4/2005
(Continued)

OTHER PUBLICATIONS

Kim et al., "Circulating Tumor Cell Microseparator Based on Lateral Magnetophoresis and Immunomagnetic Nanobeads," Analytical Chemistry, Mar. 5, 2013, pp. 2779-2786, vol. 85, No. 5.
(Continued)

*Primary Examiner* — Gailene Gabel
(74) *Attorney, Agent, or Firm* — McDonnell Boehnen Hulbert & Berghoff LLP

(57) ABSTRACT

The disclosure relates to an apparatus for segregating particles on the basis of their ability to flow through a stepped passageway. At least some of the particles are unable to pass through a narrower passageway bounded by a segregating step, resulting in segregation of the particles. The breadth of the leading edge of at least one step of the apparatus is significantly greater than the overall width of the passageway in which the step occurs, permitting high and rapid sample throughput. The apparatus and methods described herein can be used to segregate particles of a wide variety of types. By way of example, they can be used to segregate circulating tumor cells from a human blood sample.

12 Claims, 12 Drawing Sheets

Related U.S. Application Data continuation of application No. 14/077,811, filed on Nov. 12, 2013, now Pat. No. 9,631,179.

(60) Provisional application No. 61/794,468, filed on Mar. 15, 2013.

(52) U.S. Cl.
CPC ... *B01L 2200/0652* (2013.01); *B01L 2200/12* (2013.01); *B01L 2300/0816* (2013.01); *B01L 2300/0864* (2013.01)

(58) Field of Classification Search
CPC .......... G01N 2015/0288; C12N 5/0694; C12Q 1/24; B01L 3/502753; B01L 2200/12; B01L 2200/0652; B01L 2300/0816; B01L 2300/0864
See application file for complete search history.

(56) References Cited

U.S. PATENT DOCUMENTS

| | | | |
|---|---|---|---|
| 7,993,908 B2 * | 8/2011 | Hvichia | B01L 3/502761 422/534 |
| 9,631,179 B2 * | 4/2017 | Hvichia | C12N 5/0694 |
| 9,851,344 B2 * | 12/2017 | Hvichia | G01N 33/491 |
| 2011/0244443 A1 | 10/2011 | Van Rijn et al. | |
| 2015/0300939 A1 * | 10/2015 | Ma | G01N 1/4077 435/29 |

FOREIGN PATENT DOCUMENTS

| | | | | |
|---|---|---|---|---|
| WO | 2009/131645 A2 | 10/2009 | | |
| WO | WO 2009/131645 | * 10/2009 | ............. | G01N 33/49 |
| WO | 2010/011934 A2 | 1/2010 | | |
| WO | 2010/129441 A2 | 11/2010 | | |
| WO | 2011/028483 A2 | 3/2011 | | |
| WO | WO 2011/028483 | * 3/2011 | ............... | C12Q 1/24 |
| WO | 2011/066497 A2 | 6/2011 | | |
| WO | 2012/139209 A1 | 10/2012 | | |

OTHER PUBLICATIONS

Vankrunkelsven et al., "A Novel Microstep Device for the Size Separation of Cells," Electrophoresis, Wiley Interscience, DE, Jun. 2, 2004, pp. 1714-1722, vol. 25, No. 2.

European Patent Office, Intention to Grant dated Dec. 4, 2015, issued in connection with European Application No. 14159725.2, 38 pages.

European Patent Office, Extended European Search Report dated Nov. 25, 2014, issued in connection with European Application No. 14159725.2, 8 pages.

Lin et al., "Portable Filter-Based Microdevice for Detection and Characterization of Circulating Tumor Cells," Clin. Cancer Res., 2010, pp. 5011-5018, vol. 16.

Paterlini-Brechot et al., "Circulating tumor cells (CTC) detection: Clinical impact and future directions," Cancer Letters, 2007, pp. 180-204, 2007.

Vona et al., "Isolation by Size of Epithelial Tumor Cells—A New Method for the Immunomorphological and Molecular Characterization of Circulating Tumor Cells," American J. Pathology, 2000, pp. 57-63, vol. 156.

Goon et al., "Circulating Endothelial Cells, Endothelial Progenitor Cells, and Endothelial Microparticles in Cancer," Neoplasia, vol. 8, pp. 79-88 (2006).

Damani et al., "Characterization of Circulating Endothelial Cells in Acute Myocardial Infarction," Sci. Transl. Med., Mar. 21, 2012; 4(126): 126ra33.

* cited by examiner

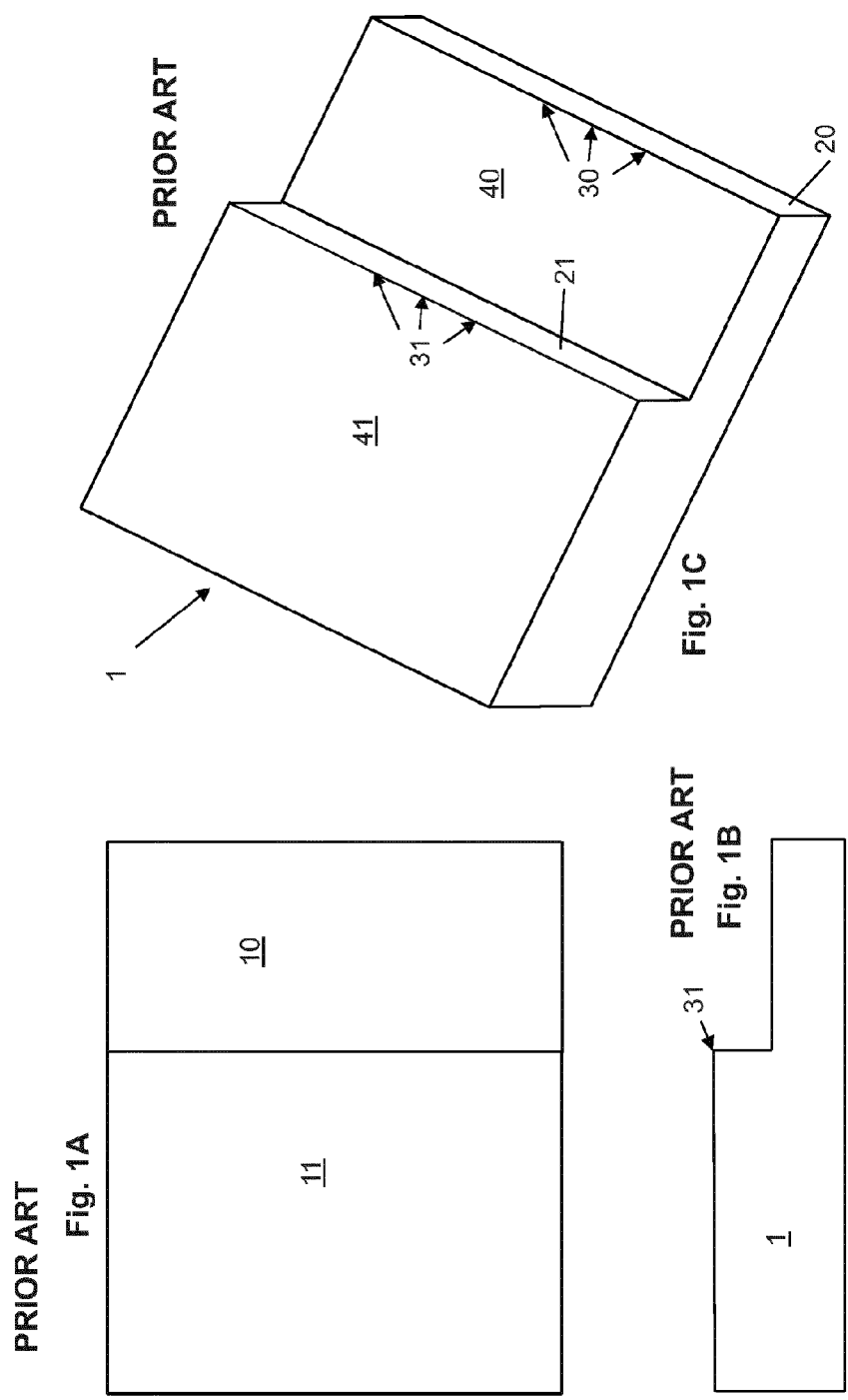

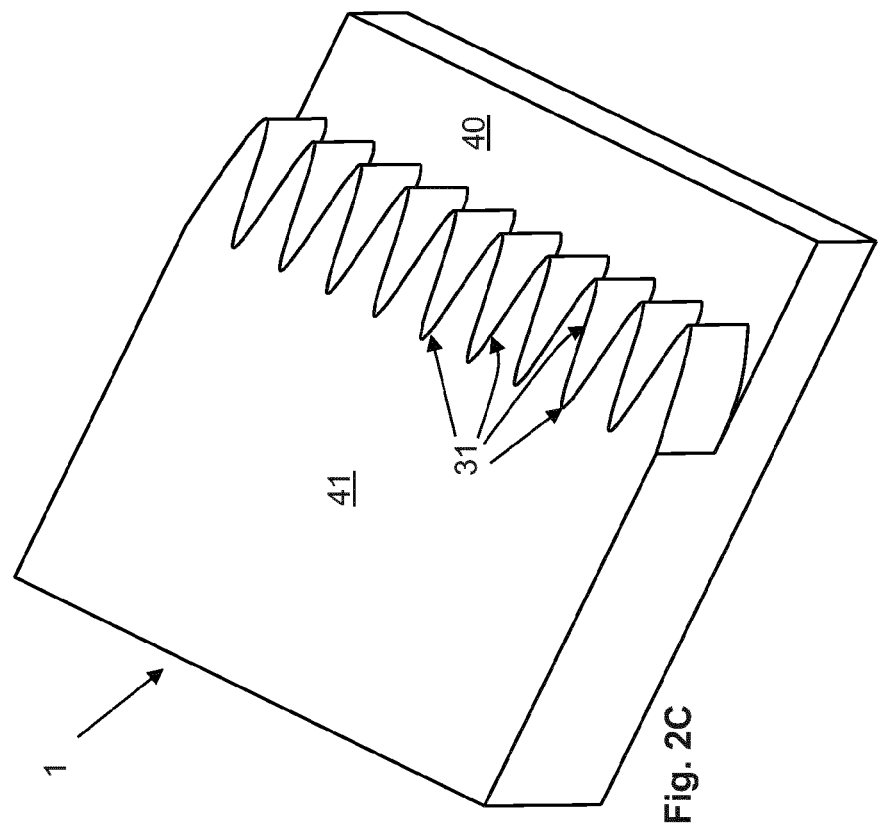
Fig. 2C
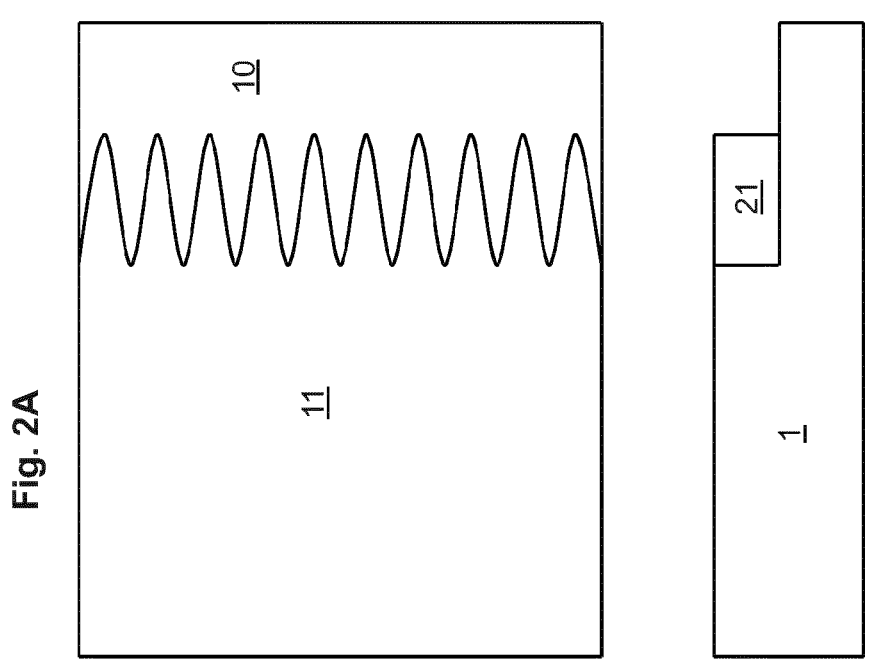
Fig. 2A
Fig. 2B

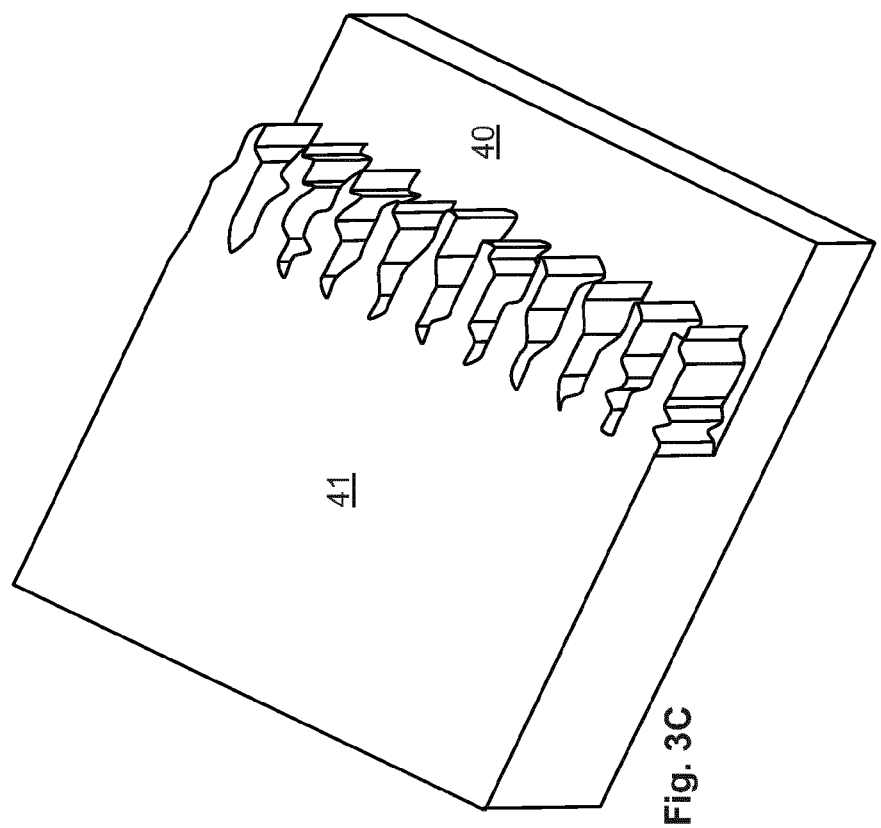
Fig. 3C
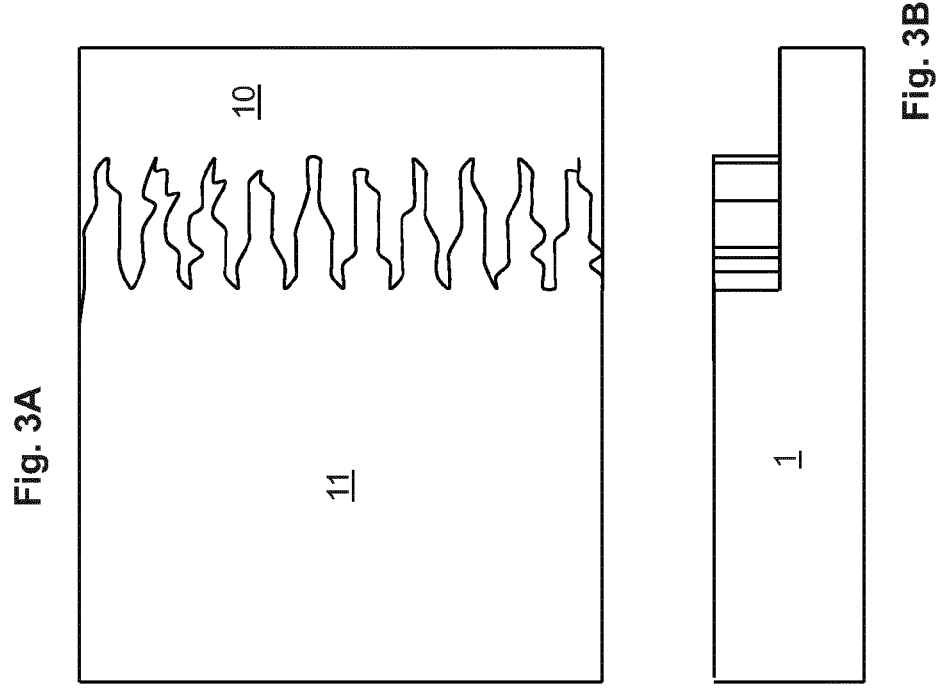
Fig. 3A
Fig. 3B

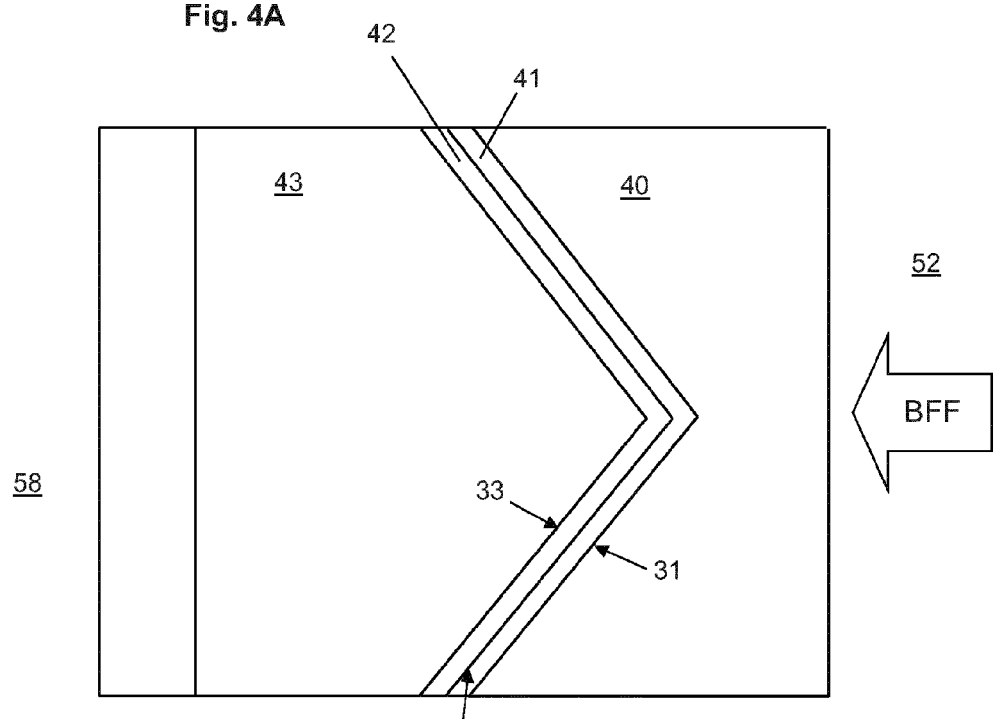
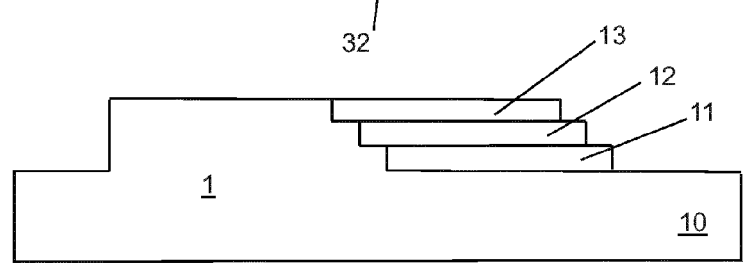

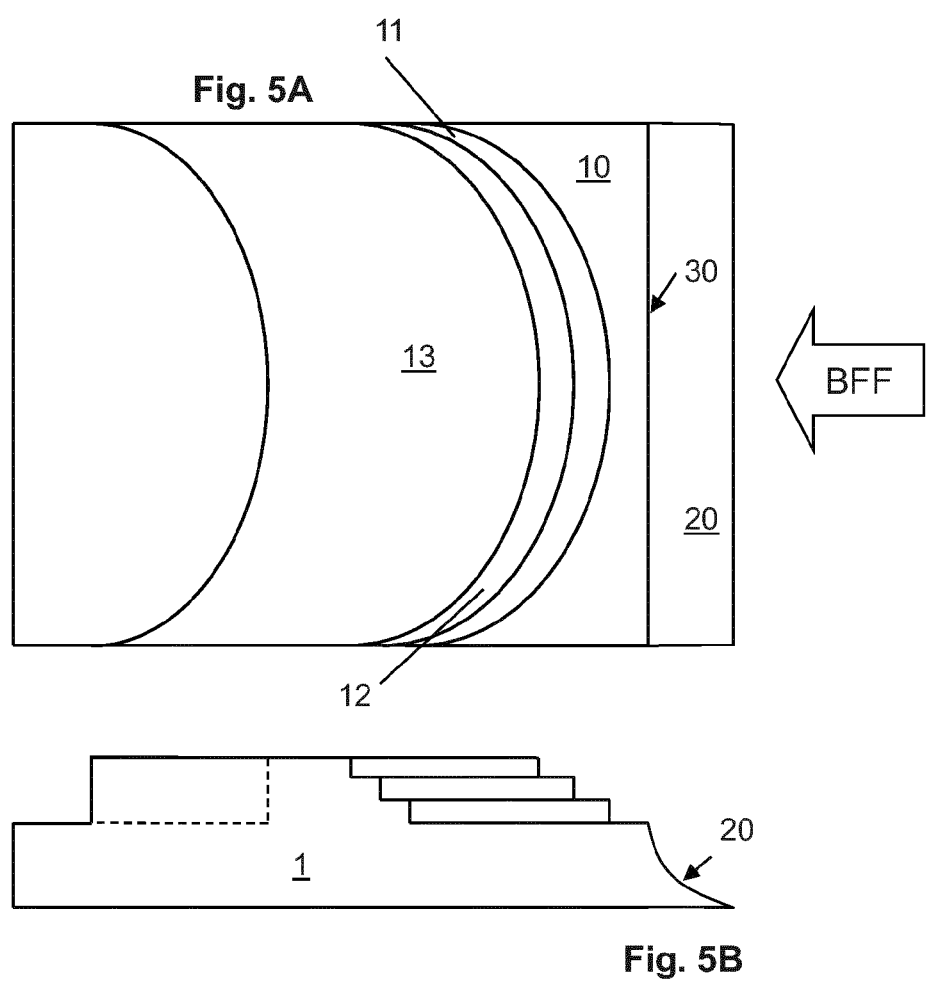

Fig. 6A
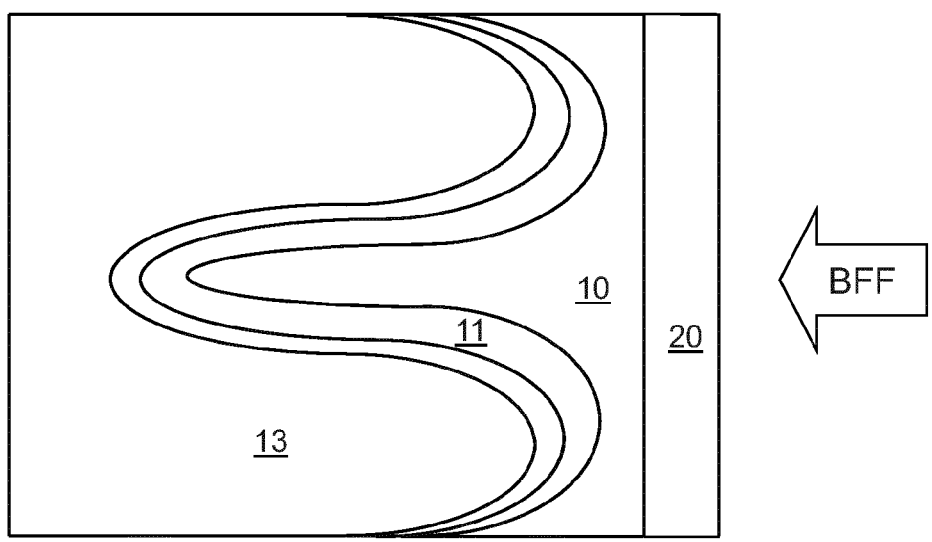
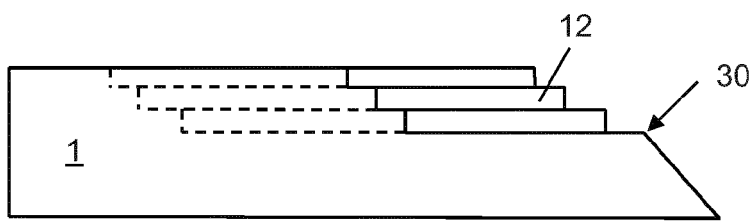
Fig. 6B

B = L + W
B = 5W

B = 2L+W
B = 5W

B = 4L+W
B = 5W

B = 8L+W
B = 5W

METHODS FOR SEGREGATING PARTICLES USING AN APPARATUS WITH A SIZE-DISCRIMINATING SEPARATION ELEMENT HAVING AN ELONGATE LEADING EDGE

CROSS-REFERENCES TO RELATED APPLICATIONS

This application is a continuation of U.S. patent application Ser. No. 15/434,249, filed 16 Feb. 2017, now U.S. Pat. No. 9,851,344, which is a continuation of U.S. patent application Ser. No. 14/077,811, filed 12 Nov. 2013, now U.S. Pat. No. 9,631,179, which claims priority to U.S. provisional patent application 61/794,468, filed 15 Mar. 2013. The foregoing applications are incorporated herein by reference.

BACKGROUND OF THE DISCLOSURE

Mechanical devices intended for manipulation of biological cells and other small particles and having structural elements with dimensions ranging from tens of micrometers (the dimensions of biological cells) to nanometers (the dimensions of some biological macromolecules) have been described. For example, U.S. Pat. Nos. 5,928,880, 5,866,345, 5,744,366, 5,486,335, and 5,427,946 describe devices for handling cells and biological molecules. PCT Application Publication number WO 03/008931 describes a microstructure for particle and cell separation, identification, sorting, and manipulation.

U.S. Pat. No. 7,993,908 describes a microscale apparatus for separating cells and other particles based on their size. The apparatus described in that patent includes a stepped separation element interposed between two regions of a void formed by a cover and body, and separation of particles within the apparatus is governed by the ability of particles initially present in one region to traverse the stepped separation element to arrive at the other region. The subject matter disclosed herein is considered an improvement upon this apparatus.

The subject matter disclosed herein can be used to segregate and manipulate biological cells, organelles, cell conglomerates, and other particles from mixed populations of particles or cells.

SUMMARY OF THE DISCLOSURE

The present disclosure relates to an apparatus for segregating smaller and larger particles. The apparatus includes a body and a cover that define a void between them. The void contains a separation element that segregates an inlet region and an outlet region of the void. Together with one or more surfaces of the void, the separation element defines a channel that fluidly connects the inlet and outlet regions by way of a separating portion. The channel has an overall width at the separating portion and a height defined by the distance between the separation element and the surface of the void. At least one of the body, the cover, and the separation element bears a segregating step disposed within and having a leading edge extending substantially completely across the separating portion of the channel. The channel is divided into an upstream portion on the inlet side of the leading edge and a substantially lamellar downstream portion on the outlet side of the leading edge. The height of the upstream portion is sufficient to facilitate passage therethrough of both larger and smaller particles. The height of the downstream portion is sufficient large to facilitate passage therethrough of the smaller particles and sufficiently small to inhibit passage therethrough of the larger particles. The breadth of the leading edge is substantially greater than the overall width of the channel at the separation region (which is normally the same width as that of the segregating step, meaning that leading edge of the segregating step is normally longer than the width of that step). The particles can be segregated by passing them through the channel and recovering particles based on their ability to traverse the segregating step.

In one embodiment, the upstream portion of the channel is substantially lamellar, meaning that it is defined by two broad surfaces that are substantially parallel to one another.

The breadth of the leading edge can be substantially (e.g., at least 100 times) greater than a characteristic dimension of the larger particles, so that many such particles can be trapped at the leading edge without substantially preventing bulk fluid flow past the leading edge. The breadth of the leading edge can also be substantially (e.g., at least 1.5, 2, 3, 4, 5, 10, 20, 50, 100, 500, 1000, 10000, or 100000 times) greater than the overall width of the channel at the separation region (or the width of the segregating step within the channel). By way of example, the height of the downstream portion (i.e., the portion of the channel of the leading edge of the segregating step) can be selected so that it is sufficiently small to inhibit passage therethrough of a selected cell type (e.g., a circulating tumor cell or human fetal stem-like cells), sufficiently large that it does not inhibit passage therethrough of a selected cell type (e.g., human red blood cells), or a combination of these.

The leading edge of any segregating step can have an angular, curved, undulating, invaginated, or irregular shape. The segregating step can have, on its inlet side, an upstream face that is substantially perpendicular to the portion of the step that defines the downstream portion of the channel.

The separation element can be integral with at least one of the body and the cover. It can also be a separate item interposed between the body and the cover. The device can have one or more supports for maintaining the height of the channel. Such supports can be disposed within the channel and extend between the separation element and the surface of the void, for example.

The disclosure also relates to methods of segregating larger and smaller particles. These methods include providing a fluid suspension of larger and smaller particles at the inlet of the apparatus described herein. Fluid is urged through the channel and one can collect at least one of i) smaller particles (e.g., red blood cells) at the outlet region, and ii) larger particles (e.g., circulating tumor cells) upstream of the leading edge of the segregating step.

The disclosure also relates to methods of diagnosing occurrence of a tumor in a vertebrate subject. These methods include steps of i) providing a blood sample obtained from the subject to the inlet region of the apparatus described herein (the height of the lamellar portion of the downstream portion of the channel is smaller than the size of a CTC), passing the sample through the channel of the apparatus, and thereafter examining the portion of the apparatus upstream of the leading edge of the segregating step for the presence of a cell. Presence of at least one cell is an indication that a tumor occurs in the subject. One or more diagnostic tests can thereafter be used to assess a characteristic of a tumor cell for at least one cell that was present upstream of the leading edge of the segregating step after passing the sample through the channel. Examples of such tests include binding the cell or an extract thereof with a tissue-specific or tumor-specific antibody, analyzing nucleic acids obtained from such a cell that was present upstream of the leading edge, or assessing the proliferative capacity of the cell.

The disclosure further relates to methods of assessing the efficacy of a tumor treatment for a subject afflicted with a tumor. These methods include isolating CTCs from blood samples obtained from the subject before and after the treatment using the methods described herein. At least one characteristic of the CTCs isolated from the samples is compared among the samples. A difference in the characteristics of CTCs (e.g., CTC concentration or number) isolated from the blood samples is an indication of the efficacy of the treatment.

The disclosure also relates to methods of reducing CTC load in a vertebrate subject. Such methods include steps of i) providing blood obtained from the subject at the inlet of the apparatus described herein (wherein the height of the lamellar portion of the downstream portion of the channel is smaller than the size of a CTC), ii) urging the blood through the channel to deplete CTCs from the blood, iii) collecting CTC-depleted blood at the outlet region, and iv) returning the CTC-depleted blood to the subject.

BRIEF DESCRIPTION OF THE SEVERAL VIEWS OF THE DRAWINGS

The foregoing summary, as well as the following detailed description of the invention, will be better understood when read in conjunction with the appended drawings. These drawings are included for the purpose of illustrating the disclosure. The disclosure is not limited to the precise arrangements and instrumentalities shown.

FIG. 1 consists of FIGS. 1A, 1B, 1C, and 1D, and illustrates a prior art separation element 1 having two integral, rectangular slab-shaped steps, including a focusing step 10 and a segregating step 11. Devices having a separation element of this sort are disclosed in U.S. Pat. No. 7,993,908, for example. FIG. 1A is an elevated view of the separation element 1 in which the rectangular shape of the face 20 of the focusing step 10 can be seen adjacent the broad face 40 thereof and the rectangular shape of the face 21 of the segregating step 11 can be seen adjacent the broad face 41 thereof. FIG. 1B is a side view of the separation element 1 shown in FIG. 1A, showing the height difference between the focusing and segregating steps (10 and 11, respectively). FIG. 1C is an orthogonal view of the separation element 1 shown in FIGS. 1A and 1B. In FIG. 1D, the height ($h_1$) of a downstream portion of the fluid channel, the height ($h_0$) of an upstream portion of the fluid channel, and the height ($h_c$) of the fluid channel itself are shown. The height ($h_1$) of the downstream portion is defined by the distance between the segregating step 11 and the cover 4, and the height ($h_0$) of the upstream portion is defined by the distance between the focusing step 10 and the cover 4.

FIG. 2 consists of FIGS. 2A, 2B, and 2C and illustrates a separation element 1 having a rectangular slab-shaped focusing step 10 and a segregating step 11 having a slab shape but having an undulating face 21 and leading edge 31. FIG. 2A is an elevated view of the separation element 1 in which the undulating shape of the face 21 of the segregating step 11 can be seen adjacent the broad face 41 thereof. FIG. 2B is a side view of the separation element 1 shown in FIG. 2A, showing the height difference between the focusing and segregating steps (10 and 11, respectively). FIG. 2C is an orthogonal view of the separation element 1 shown in FIGS. 2A and 2B.

FIG. 3 consists of FIGS. 3A, 3B, and 3C and illustrates a separation element 1 having a rectangular slab-shaped focusing step 10 and a segregating step 11 having a slab shape but having an irregular face and leading edge. FIG. 3A is an elevated view of the separation element 1 in which the rectangular shape of the face of the focusing step 10 can be seen adjacent the broad face 40 thereof and the irregular shape of the face of the segregating step 11 can be seen adjacent the broad face 41 thereof. FIG. 3B is a side view of the separation element 1 shown in FIG. 3A, showing the height difference between the focusing and segregating steps (10 and 11, respectively). FIG. 3C is an orthogonal view of the separation element 1 shown in FIGS. 3A and 3B.

FIG. 4 consists of FIGS. 4A, 4B, and 4C, and illustrates a separation element 1 having a rectangular focusing step 10 and three steps atop it and downstream (relative to BFF) from its leading edge. Each of the first segregating step 11, second segregating step 12, and third segregating step 13 has a chevron-shaped leading edge (leading edges 31, 32, and 33, respectively. Bulk fluid flow BFF direction is indicated. FIG. 4A is an elevated view of the separation element 1. FIG. 4B is a side view of the separation element 1 shown in FIG. 4A, showing the height differences among the steps. A recessed portion of the separation element 1 downstream of steps 11-13 forms part of an outlet passageway by way of which material that has traversed all of steps 10-13 can be carried away from the separation element 1. In FIG. 4C, the heights ($h_3$, $h_2$, and $h_1$, respectively) of serial downstream portions of the fluid channel, the height ($h_0$) of an upstream portion of the fluid channel, and the height ($h_c$) of the fluid channel itself are shown. The height ($h_3$) of a third downstream portion is defined by the distance between the third segregating step 13 and the cover 4. The height ($h_2$) of a second downstream portion is defined by the distance between the second segregating step 12 and the cover 4. The height ($h_1$) of a first downstream portion is defined by the distance between the first segregating step 11 and the cover 4. The height ($h_0$) of the upstream portion is defined by the distance between the focusing step 10 and the cover 4.

FIG. 5 consists of FIGS. 5A and 5B and illustrates a separation element 1 having a focusing step 10 having a curved transitional face 20 that extends completely across the separation element 1 and three segregating steps atop it and downstream (relative to BFF) from the focusing step 10. Each of the first segregating step 11, second segregating step 12, and third segregating step 13 has a curved leading edge, meaning that the breadth of the leading edge of each of segregating steps 11-13 is greater than its width (unlike the length of the leading edge 30 of focusing step 10, which is equal to its width). Bulk fluid flow BFF direction is indicated. FIG. 5A is an elevated view of the separation element 1. FIG. 5B is a side view of the separation element 1 shown in FIG. 5A, showing the height differences among the steps. A recessed portion of the separation element 1 downstream of steps 10-13 forms part of an outlet passageway by way of which material that has traversed all of steps 10-13 can be carried away from the separation element 1.

FIG. 6 consists of FIGS. 6A and 6B and illustrates a separation element 1 having a rectangular focusing step 10 and three segregating steps atop it and downstream (relative to BFF) from its leading edge. Each of the first segregating step 11, second segregating step 12, and third segregating step 13 has a serpentine leading edge. Bulk fluid flow BFF direction is indicated. FIG. 6A is an elevated view of the separation element 1. FIG. 6B is a side view of the separation element 1 shown in FIG. 6A, showing the height differences among the steps.

DETAILED DESCRIPTION

Figure 1D:
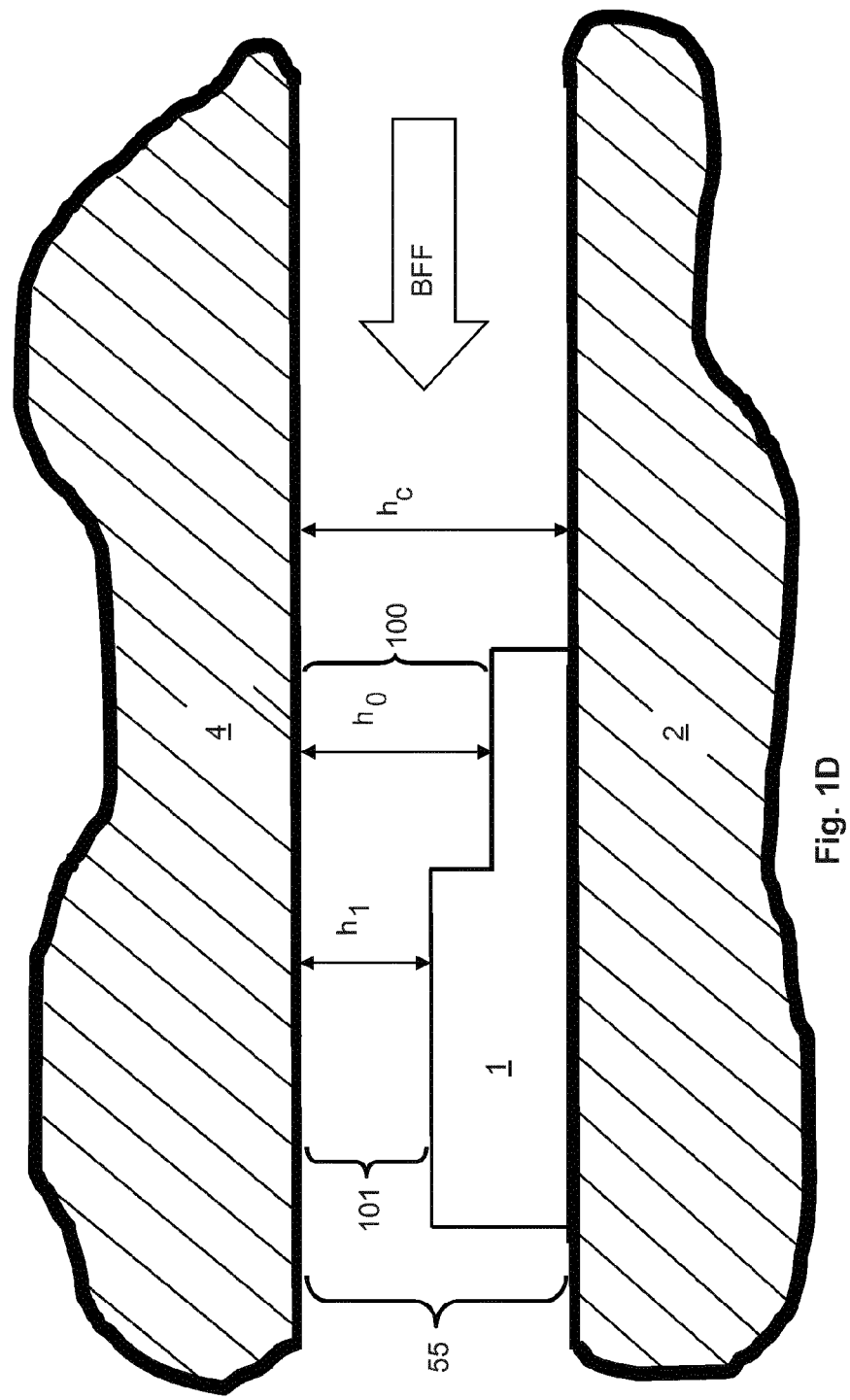
FIG. 1D is a cross-sectional view of the separation element 1 disposed in a fluid channel defined by a gap between a cover 4 and the body 2 of an apparatus described herein.

The disclosure relates to an apparatus for segregating particles on the basis of their ability to traverse a passageway. Particles (e.g., particles suspended in a liquid or gaseous fluid or particles in a vacuum) are moved through a stepped passageway 55 defined by a separation element 1 in the apparatus. The stepped passageway 55 connects portions of a void 50 defined by a body 2 and a cover 4, and separation element 1 is present within the void 50 and separates inlet and outlet regions (52 and 58, respectively) regions of the void 50. The separation element 1 may be a discrete element, or it may be attached to or integral with one of body 2 and cover 4.

The stepped passageway 55 fluidly connects the inlet region 52 and the outlet region 58 of the void 50, and contains at least one segregating passageway 101 that has a narrow dimension defined by the distance between the face 41 of a (first) segregating step 11 and another portion of the (first) segregating passageway 101, such as the face of the body 2 or the cover 4. Only some particles in the fluid are able to move into the segregating passageway 101. The net result is that some particles can move through the entire stepped passageway 55, while other particles are retained within the apparatus, such as upstream of the segregating passageway 101. Segregation of particles is thus achieved. Movement of particles can be motivated by fluid flow, gravity, vibration, or any combination of these, for example.

In contrast to analogous devices disclosed, for example, in U.S. Pat. No. 7,993,908 (illustrated in FIG. 1), the leading edge 31 and transitional face 41 of at least one of the segregating steps of the devices described herein has a breadth substantially greater (e.g., by a factor of at least 1.5, 2, 10, 25, 100, 1000, 10,000, or 100,000) than the width of the segregating step (i.e., greater than the width of the stepped passageway 55 in which the segregating step 11 is disposed. Because separation of particles in bulk fluid flowing past a segregating step 11 tends to occur mostly at the leading edge and face 21 of the step, increasing the breadth of these, relative to the width of the segregating step 11 and passageway can have several beneficial effects.

Particles flowing past a segregating step 11 in a bulk fluid will necessarily have a size, in at least one dimension, not greater than the height of the segregating passageway 101 above that segregating step 11 (i.e., the narrow dimension of the segregating passageway; otherwise the particles would be unable to pass therethrough with the bulk fluid). Likewise, particles having dimensions greater than the height of the segregating passageway 101 above a segregating step 11 will cease to flow with bulk fluid at or near the leading edge 31 or the transitional face 21 of the segregating step 11 and will tend to accumulate there. Increasing the breadth of the transitional face 21 and leading edge 31 beyond the overall width of the passageway in which the segregating step 11 is disposed permits multiple particles to be accommodated at the leading edge 31 or elsewhere along the transitional face 21 (e.g., if the face is sloped). Thus, the apparatus in which the leading edge has a breadth greater than the overall width of the segregating passageway 101 can be used to capture one or more size-segregated particles at or near the leading edge 31 of the segregating step 11. As the breadth of the leading edge 31 of the segregating step 11 increases, a greater number of size-segregated particles can be captured at the transitional face 21 thereof without clogging the device. It is desirable that the ratio of the breadth of a segregating step be substantially greater (e.g., at least 1.5-fold, and more preferably 2-, 3-, 4-, 5-, 10-, 20-, 50-, 100-, 500-, or 1000-fold greater) than the width of the passageway that bounds the ends of the leading edge of the segregating step.

Figure 4C:
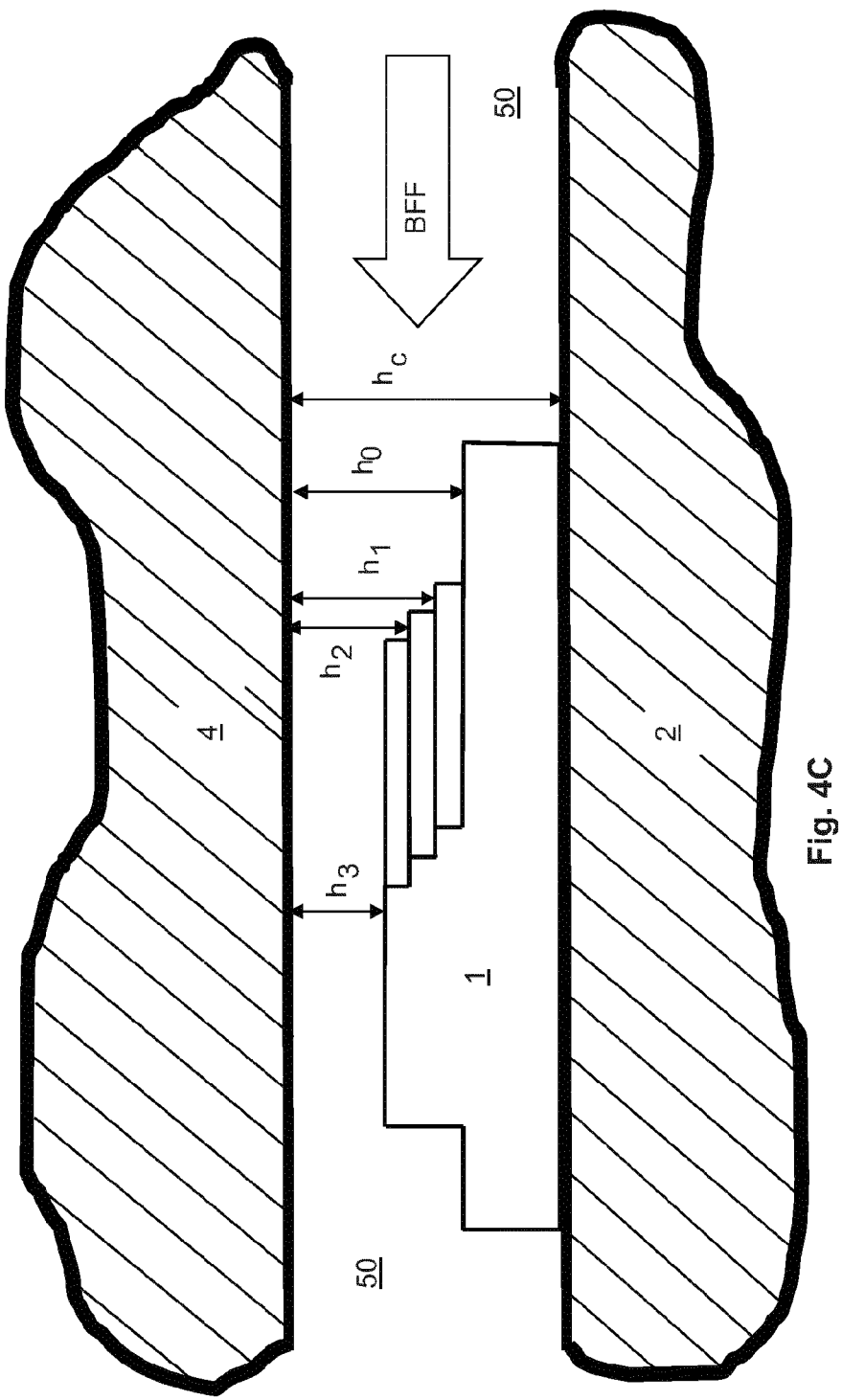
FIG. 4C is a cross-sectional view of the separation element 1 disposed in a fluid channel defined by a gap between a cover 4 and the body 2 of an apparatus described herein.
Figure 7A:
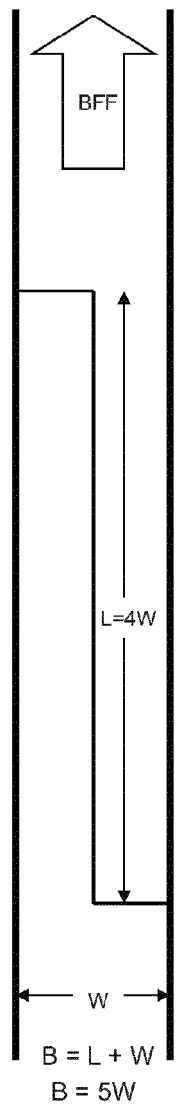
In FIG. 7A, step height rises across half the fluid channel at a relatively upstream position and across the other half of the fluid channel at a relatively downstream position, with the step face extending between those two positions. The length (L) of the extended step face is equal to four times the width (W) of the fluid channel in FIG. 7A, yielding a total B of the step equal to 5W.
Figure 7B:
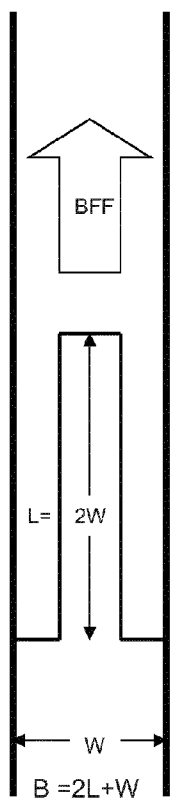
In FIG. 7B, the step has two portions extending between an upstream position and a downstream position. Although the length of the step face extension in the direction of BFF is only 2W, there are two such extensions. As a result the total breadth of the face in FIG. 7B is 2×2W+W, or 5W. Similarly, the step shown in FIG. 7C, which has three portions extending between upstream and downstream positions (i.e., four step face extensions of length W) exhibits a B of 4×W+W, or 5W. The step shown in FIG. 7D, which has five portions extending between upstream and downstream positions (i.e., eight step face extensions of length W/2) exhibits a B of 8×W/2+W, or 5W. Of note, L of steps having equal B decreases with increasing invagination of the steps. This illustrates that miniaturization of particle separation functionality of a step can be achieved by increasing the complexity (B/L) of the step face.
Figure 7C:
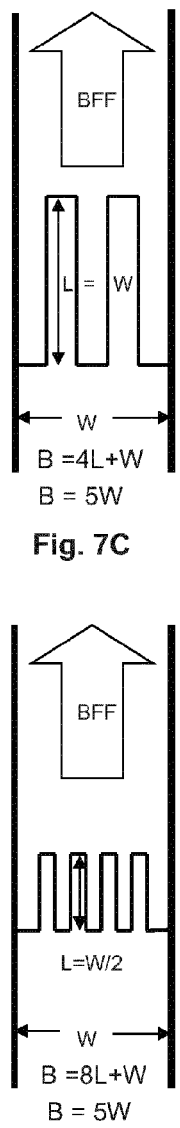
FIG. 7 consists of FIGS. 7A, 7B, 7C, and 7D (which are drawn approximately to scale relative to one another) and illustrates four step configurations having equal breadth (B) in a fluid channel indicated by heavy lines. The direction of bulk fluid flow (BFF) is indicated, and step height increases from the upstream to the downstream side of the step, which is indicated by a line extending across the fluid channel in the figures.
Figure 7D:
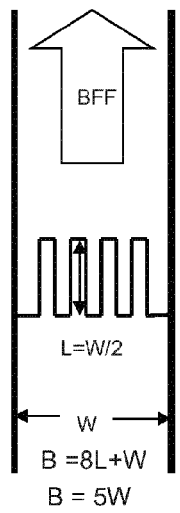

In order to accommodate a leading edge 21 having a breadth greater than the width of the segregating passageway 101, the leading edge 21 and the transitional face 31 of a segregating step 11 must not extend straight across the narrowest width of the segregating passageway 101. The leading edge can be straight (e.g., extending obliquely across the passageway 101 in a direction other than the narrowest dimension thereof) or composed of multiple straight segments (see FIGS. 4 and 7). The leading edge 21 can also be curved (See FIG. 5), invaginated (See FIGS. 2, 3, and 6), or meandering (See FIG. 3) in shape, thereby increasing its breadth (and that of its corresponding segregating step 11 and transitional face 21) relative to the width of the segregating passageway 101. As a result of such leading edge shapes, the capture capacity of the apparatus can be increased, relative to prior art devices in which segregating steps 11 extended directly across the width of the segregating passageway 101.

In one embodiment, the leading edge of the step is highly curved (e.g., has many invaginations, such as the invagination shown in segregating steps 11-13 in FIG. 6), so that its breadth is significantly greater than the overall width of the passageway in which the step is contained. By way of example, FIGS. 4, 5, and 6 illustrate a four-step separation element 1 that can be accommodated within a passageway having a substantially rectangular cross section. In FIGS. 4, 5, and 6, the separation element 1 has an overall width equal to the width (i.e., in the direction perpendicular to bulk fluid flow BFF) of the segregating passageway 101. The separation element 1 in each of these figures includes a focusing step 10 that extends directly across the segregating passageway 101 (like steps in prior art devices) and thus has a breadth equal to the overall width of the passageway.

In FIG. 4, the leading edge of each of segregating steps 11-13 has a breadth greater than the overall width of the segregating passageway 101—if the vertex of the chevron-shaped leading edge of each step is a right angle, then the length of the leading edge of each step is (by application of the Pythagorean equation) equal to twice the square root of (the square of the width of the passageway divided by two) (i.e., if the width of the segregating passageway 101 is one unit, then the breadth of each step is about 1.4 units).

In FIG. 5, the breadth of the leading edge of each of segregating steps 11-13 is greater than the overall width of the segregating passageway 101, on account of the curvature of the leading edge of each step.

In FIG. 6, the breadth of the leading edge of each of segregating steps 11-13 is longer still, owing to the curvature and invagination of each step.

The geometries shown in FIGS. 4-6 are for illustrative purposes. Step leading edges can have innumerable geometric shapes. The shapes shown in those figures simply illustrate the concept that increasing the complexity (especially 'folding' or invagination) of the leading edge can cause the breadth of the leading edge of any step to greatly exceed the overall width of the passageway within which the step occurs. In another embodiment of the separation element shown in FIGS. 4-6, the separation element lacks focusing step 10 and the segregating steps 11-13 are integral with three adjacent walls of the substantially rectangular segregating passageways 101-103 in which the separation element 1 is disposed.

Particles unable to traverse a segregating step can be urged in the direction of bulk fluid flow along the leading edge of the segregating step. Thus, for example, particles that are able to traverse the focusing step, but are unable to traverse the segregating steps of the device shown in FIG. 6 will tend to be urged by bulk fluid flow toward the central invagination in the segregating steps and toward the peripheral edges of those steps. Although not shown, the shapes of the leading edges of the segregating steps illustrated in FIGS. 4 and 5 can be inverted relative to the direction of BFF shown in those figures (i.e., so that the apices of the chevron-shaped and curved steps lie downstream from the edges of the steps). Steps can thus be shaped to facilitate or promote accumulation of particles at selected locations along their leading edges.

Particles captured at the leading edge 31 or along the transitional face 21 of a segregating step 11 (i.e., a step past which some, but not all, particles in a bulk fluid can move with the bulk fluid flowing past the step) will tend to occlude fluid flow past the step at or on which they are captured (i.e., at the position at which their movement with the bulk fluid stops or is substantially inhibited). If captured particles occlude fluid flow past a substantial portion (e.g., >0.01%, >0.1%, >1%, >10%, >50%, >90%, or >99%) of the stepped passageway, this will decrease the throughput of the segregating passageway 101 (i.e., the volume of fluid that can be passed through the narrow passageway in a unit of time at a selected fluid pressure drop across the step) can be significantly diminished.

By increasing the breadth of the leading edge 31 of at least one segregating step 11 (i.e., relative to the overall width of the space within which the segregating passageway 101 is contained), captured particles will individually occupy a smaller percentage of the flow area of the segregating passageway 101, reducing flow occlusion and increasing the ability of the apparatus to maintain a near-constant throughput. Constant throughput can reduce the need for complicated or expensive fluid flow control equipment, since the pressure drop across the apparatus should remain substantially constant so long as throughput remains substantially constant. A very broad step leading edge 31 can therefore significantly reduce the tendency of the apparatus to experience decreased throughput for samples having significant numbers of captured particles. Such apparatus can also capture a greater number of size-segregated particles without exhibiting significantly decreased throughput.

The subject matter described herein is complementary to the subject matter disclosed in U.S. provisional patent applications No. 60/306,296, No. 61/125,168, No. 61/236,205, and No. 61/264,918 and in international patent applications no. PCT/US2002/022689, no. PCT/US2009/002421, no. PCT/US2010/046350, and no. PCT/US2010/058172, each of which is incorporated herein by reference.

Definitions

As used herein, each of the following terms has the meaning associated with it in this section.

For fluid flowing through a passageway in which a separation element 1 as described herein is disposed, the "height" of the passageway is the minimum distance between the surfaces of the passageway between which the separation element 1 is interposed. For example, in each of FIGS. 1D and 4C, a separation element 1 is interposed between a body 2 and a cover 4. The minimum distance between the parallel faces of the body 2 and cover 4 defines the height ($h_c$) of the passageway. Also visible in these figures are the height (h0) of the passageways above the focusing steps 10 of the separation elements 1 and the heights ($h_1$, $h_2$, and $h_3$) of the segregating passageways 101, 102, and 103 above segregating steps 11, 12, and 13, respectively. It is not critical that the 'height' dimension be oriented vertically relative to gravity during operation of the devices described herein.

A "focusing" step is merely a step which is disposed in (and preferably extends most of the way or completely across) the channel on the inlet side of a segregating step. A focusing step essentially directs fluid flow through the channel toward the portion of the narrow passageway defined by the segregating step, reducing potential areas of "dead volume" in which little or no local fluid flow occurs.

The channel should have a greater height on the inlet side of the focusing step than on its outlet side, such as with an inclined focusing step, or the focusing step can have a more staircase-like conformation, including multiple steps. Devices described herein need not include a focusing step, but inclusion of a separating step can be important in embodiments in which minimization of dead volume (and retention therein of particles intended to pass beyond the segregating step(s)) is desired.

The "width" of a passageway in which a separation element 1 as described herein is disposed is the minimum distance, in the direction perpendicular to the direction of bulk fluid flow through the passageway (i.e., the overall general direction of such flow, ignoring localized flow redirection induced by step geometries) and perpendicular to the height of the passageway, between opposite faces of the passageway. For example, the width of a passageway is indicated as "W" in FIG. 7 for each of four passageways containing steps of various geometries. Further by way of example, the width dimension of the stepped passageways 55 depicted in FIGS. 1D and 4C extend perpendicularly out of the figure. The "width" of a step is assessed in the same direction as the width of a passageway in which the step is disposed; thus, the width of a step that extends completely across the width a passageway is equal to the width of the passageway (even though the breadth of the leading edge of the step may be significantly greater than the width of the step owing, for example, to curvature or invagination of the leading edge).

The "breadth" of the leading edge 31 of a segregating step 11 is the length of the leading edge 31, measured following the curvature of the step. If the leading edge 31 is envisioned as an inflexible cord, the breadth of the leading edge is the length of the cord when it is pulled taut. Thus, the breadth of the leading edge of a curved or invaginated step can be significantly greater than the width of the step. This is illustrated in FIGS. 7A-7D, in which four leading edges 31 having a length 5W are configured in a variety of conformations, each leading edge substantially exceeding the width (W) of the stepped passageway 55 in which it is disposed.

The "broad face" of a step is the portion of a step that exists at a topographically altitude higher than a reference surface with respect to which the step exists. The broad face of a step described herein will generally, but need not, be planar.

The "transitional face" of a step is the portion of the step that bridges its broad face and the reference surface. The transitional face preferably has a smooth or flat contour, and can be a surface perpendicular to both the reference surface and the broad face 41, as shown for transitional face 21 in FIG. 1. Transitional faces can also be inclined planar surfaces (see transitional face 20 in FIG. 6) or curved (see transitional face 20 in FIG. 5).

The "leading edge" 31 of a step is the portion of the step at which its broad face 41 meets its transitional face 21, for example as shown in FIG. 1.

The "flow area" of a passageway is a cross-section of the passageway taken in a plane perpendicular to the direction of bulk fluid flow in the passageway.

Detailed Description

The disclosure relates to an apparatus for segregating particles on the basis of their ability to flow through a segregating passageway 101 having a minimum dimension (height) defined by the separation between a segregating step 11 of a separation element 1 and a surface of a void 50 in which the separation element is disposed. The apparatus includes a separation element 1 disposed in a void 50 formed by a body 2 and cover 4. Within the void 50, the separation element 1 separates an inlet region 52 of the void from an outlet region 58 of the void. The inlet and outlet regions are in fluid communication by way of a stepped passageway 55 defined by the separation element 1 and one or both of the body 2 and cover 4. One or more segregating steps 11 formed in the separation element 1 define one or more segregation passageways 101. Fluid that flows between the inlet and outlet regions passes through the stepped passageway 55, including through at least a first segregation passageway 101.

In operation, particles in an inlet region 52 of the void 50 pass into the stepped passageway 55 and, if they are able, into the segregating passageway 101. Particles in the segregating passageway 101 can pass to the outlet region 58 of the void 50. Cells that are not able to pass into or along the segregating passageway 101 do not reach the outlet region 58. In this way, particles able to reach the outlet region 58 are segregated from particles that are not able to reach the outlet region 58. The two populations of particles can be separately recovered from the apparatus. For example, particles at the outlet region 58 can be recovered in a stream of liquid withdrawn from the outlet region 58 (e.g., by way of an outlet port or by way of a catheter inserted into the outlet region 58). Particles unable to pass through the segregating passageway 101 to the outlet region 58 can be recovered by flushing them, in the reverse direction, through the stepped passageway 55 and into the inlet region 52. Such particles can be withdrawn from the inlet region 52. Alternatively, particles unable to pass through the segregating passageway 101 to the outlet region 58 can be left in the apparatus or recovered by disassembling the apparatus.

The apparatus described herein can be used in a wide variety of applications. In addition to segregating particles from a mixed population of particles, the device can be used in applications in which one or more of the segregated particle populations are identified or further manipulated, for example. The construction and operation of the apparatus resist clogging by the particles being segregated, relative to devices previously used for particle separation.

By way of example, the apparatus can be used to isolate tumor cells from a mixed suspension of cells, such as to isolate circulating tumor cells (CTCs) present in the blood of a human or other vertebrate subject. The apparatus can also be used to isolate fetal cells from the blood of a woman carrying (or who previously carried) a fetus. The apparatus can furthermore be used to isolate from a mixed suspension of cells substantially any cell(s) that can be differentiated from others in the suspension on the basis of their size, their compressibility, or a combination of these.

Parts and portions of the apparatus are now discussed separately in greater detail.

The Body and Cover

The apparatus has a body 2 and a cover 4 defining a void 50 therebetween. A portion of the void 50, defined in part by the separation element 1, is a stepped passageway 55. The stepped passageway 55 is also defined by a surface of the body 2, a surface of the cover 4, or by a combination of these, that is opposed to one or more stepped surfaces (e.g., 31 and 32) of the separation element 1. In order to simplify construction of the apparatus, most or all of the stepped passageway-defining surfaces can be formed or machined into a separation element 1 that is an integral part formed in a recess of the cover 4 or the body 2, the recessed portion being surrounded by a flat surface, so that the opposed surface of the body 2 or the cover 4 need only be another flat surface in order to form the void 50 and enclose the separation element 1 therein upon contact between the flat surfaces of the body 2 and cover 4.

The general format of the body 2 and cover 4 having an interposed separation element 1 is discussed generally in documents that are incorporated herein by reference, and substantially any arrangement described therein can be used for the apparatus described here. Described herein are elements of the separation element 1 that are not disclosed in those documents.

The body 2, the cover 4, or both can define an inlet port through which fluid can be introduced into or withdrawn from the void 50. For example, the body 2 can define an inlet port that fluidly communicates with the inlet region 52. Fluid introduced into the inlet port can flow into the inlet region 52, displacing fluid already there (because the void is sealed) into the stepped passageway, and thence sequentially into the first passageway 51, the second passageway 52, and the outlet region 58. Particles suspended in fluid in one of these regions and passageways can be carried into a downstream region or passageway if the particle can flow through the present and intervening passageways and regions. Similarly, withdrawal of fluid from the outlet region 58 by way of an outlet port formed in the body 2 can induce fluid flow from passageways in fluid communication with the outlet region 58 and from passageways and regions in fluid communication therewith.

Ports can be simple holes which extend through the cover or body, or they can have fixtures (burrs, rings, hubs, or other fittings) associated with them for facilitating connection of a fluid flow device to the port. The body 2, cover 4, or both can define an inlet port in the inlet region 52 of the void 50, an outlet port in the outlet region 58 of the void 50, or both an inlet port and an outlet port. Fluid can be introduced into the inlet region 52 through the inlet port. Fluid can be withdrawn from the outlet region 58 through the outlet port. Continuous introduction of fluid into the inlet region 52 and simultaneous withdrawal or emission of fluid from the outlet region 58 can create a continuous flow of fluid through the apparatus. Similarly, continuous withdrawal of fluid from the outlet region 58 and simultaneous influx or introduction of fluid into the inlet region 52 can create continuous flow.

The Void

The body 2 and the cover 4 form a void 50 when they are assembled. The void 50 has an inlet region 52, an outlet region 58, and a separation region interposed between the inlet region 52 and the outlet region 58. A separation element 1 is disposed within the separation region and, together with the body 2, the cover 4, or both, defines a stepped passageway 55. The stepped passageway 55 includes at least a first segregating passageway 101 that is defined by at least a first segregating step 11 in the separation element 1. The stepped passageway 55 can include any number of additional segregating steps, each of which can define an additional segregating passageway in the void. Preferably, the only fluid path connecting the inlet and outlet regions 52 and 58 is the stepped passageway 55, although that stepped passageway can be separated into multiple stepped passageways, arranged in series, in parallel, or in some combination of these. Likewise, multiple devices as described herein can be operated in series (e.g., to selectively capture particles in selected size ranges) or in parallel (e.g., to enhance cell capture capacity).

During operation of the device, at least the inlet region 52, the outlet region 58, and the stepped passageway of the void 50 are filled with a fluid. Preferably, the entire void 50 is filled with fluid during operation. In one embodiment, the only fluid path that connects the inlet region 52 and the outlet region 58 is the stepped passageway. Particles present in the inlet region 52 can enter the stepped passageway 55. The void (i.e., as defined by one or more of the body, cover, and separation element) can be formed so as to taper in the direction of (or opposite) bulk fluid flow from the inlet region toward the stepped passageway. Such void shapes can focus particles flow toward the stepped passageway, maintain fluid linear flow velocity through the shaped region within a desired range (e.g., substantially constant), facilitate viewing of particles passing therethrough, or have other beneficial consequences.

Particles present in the stepped passageway 55 can enter and pass through the first segregating passageway 101 unless they are excluded by the height (i.e., the narrow dimension) of the first segregating passageway 101, or unless their movement through the first segregating passageway 101 is inhibited by particles which block that passageway (e.g., cells immobilized at or upstream from the leading edge 31 of the first segregating passageway 101. Particles which pass through the first segregating passageway 101 can enter the outlet region 58 and thence be recovered. Movement of particles within the apparatus can be induced by fluid flow through the apparatus, by intrinsic motility of the cells, or a combination of the two. Over time, particles unable to enter the first passageway 51 will be segregated in the inlet region 52; particles able to traverse the first segregating passageway 101 will be segregated in or upstream from the stepped passageway 55; particles able to enter the first segregating passageway 101 but unable to freely move therethrough will be segregated in the first segregating passageway 101; and particles able to move through first segregating passageway 101 will be segregated in the outlet region 58 (or in fluid withdrawn or emitted from the outlet region 58).

Particles segregated in this manner can be recovered (using any of a variety of known methods, including some described herein) from their respective locations. By way of example, a catheter can be inserted into a region or passageway (e.g., the inlet region 52 or first segregating passageway 101) of the apparatus, and particles present therein can be withdrawn by inducing suction in lumen of the catheter. Further by way of example, backflushing (i.e., fluid flow from the outlet region 58 in the direction of the inlet region 52) can be used to collect particles present in one or more of the inlet region 52 or the first segregating passageway 101.

The Separation Element

The separation element 1 of the devices described herein can be substantially the same as those described previously in U.S. Pat. No. 7,993,908, in PCT publication WO 2011/066497, or elsewhere, but includes an additional feature. The separation element 1 of the devices described herein include at least one segregating step 11 that has a leading edge 31 with a breadth significantly greater than (e.g., 1.5×, 2×, 3×, 4×, 5×, 10×, 20×, 50×, 100×, 500×, 1,000×, 10,000×, or 100,000× greater than) the overall width of a passageway within which the segregating step occurs. Put another way, the shape of the leading edge of at least one step of the separation element 1 is such that the breadth of that leading edge is substantially greater than the overall width of the step. Put yet another way, the breadth of the leading edge of the step, assessed along its contour, is greater than the shortest linear distance between the two endpoints of the step edge (i.e., regardless of whether the step edge follows that shortest line). By way of example, the leading edge can be curved (see, e.g., FIG. 5), invaginated (see, e.g., FIG. 6), angular (see, e.g., FIG. 4), serpentine (see, e.g., FIG. 3), or irregular (see, e.g., FIG. 5). The upper limit of the ratio of step breadth to passageway width is bounded substantially only by the tolerance of the manufacturing methods used to form the step and the size of the particles that pass the step.

Figure 8:
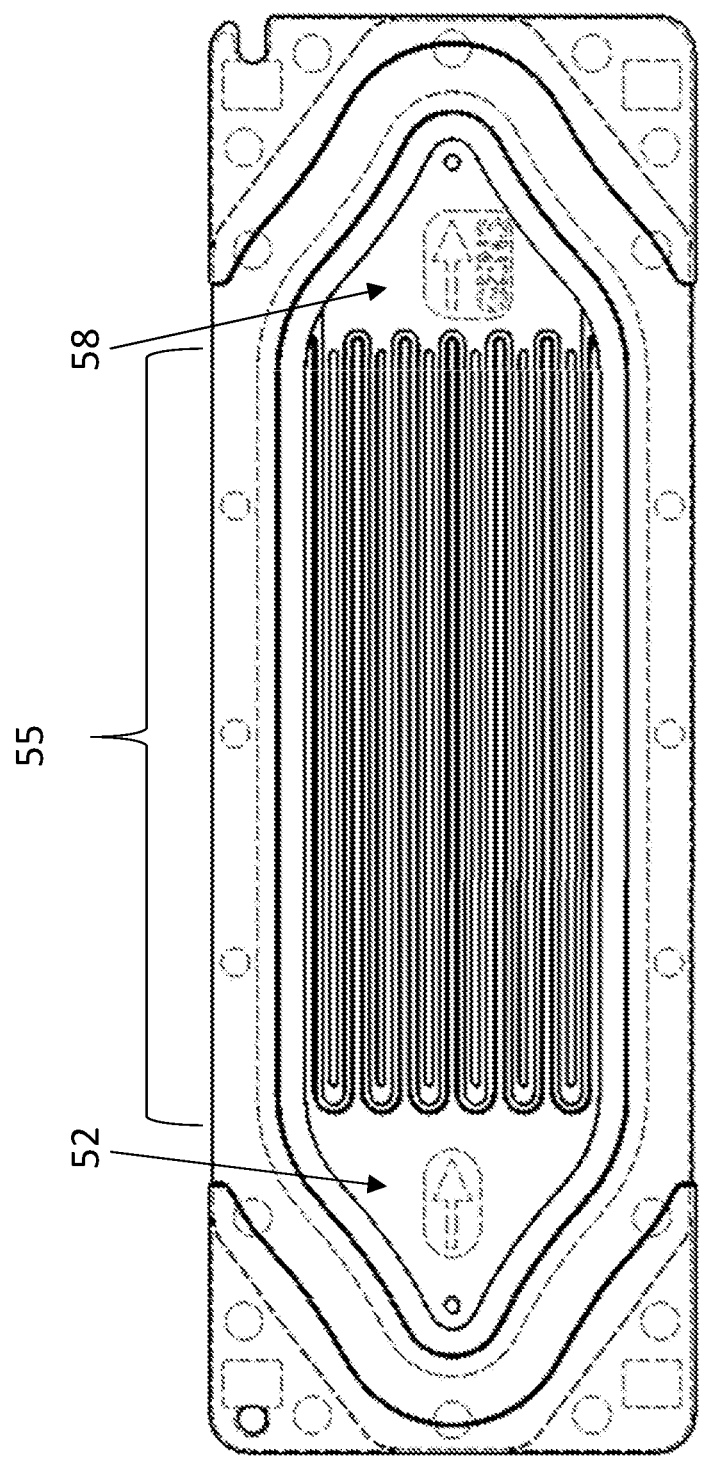
FIG. 8 is an embodiment of a particle segregation apparatus as described herein constructed to have a size approximately equal to a common microscope slide. Inlet and outlet regions 52 and 58 are shown, as is the separation portion 55 of the channel that extends between inlet and outlet regions 52 and 58.
Figure 9:
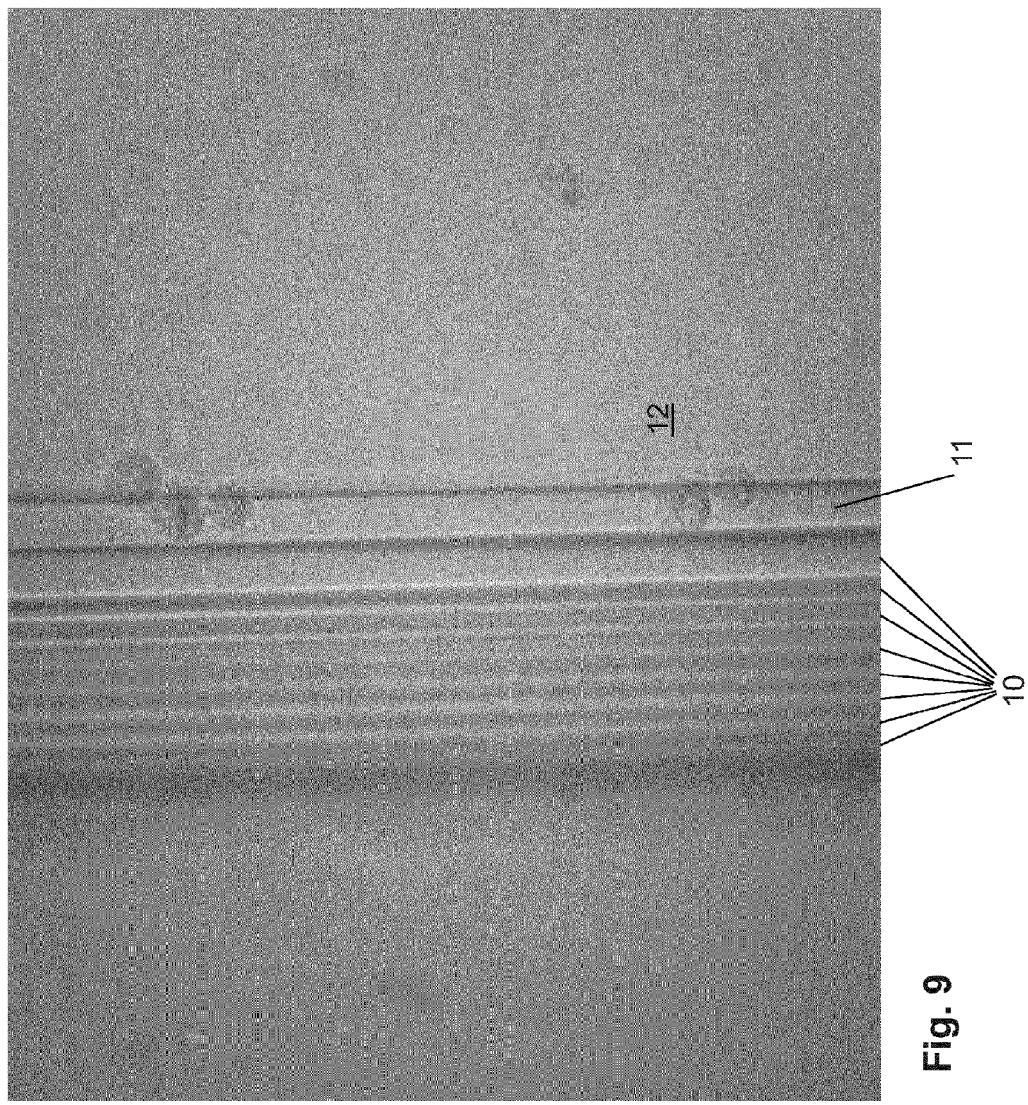
FIG. 9 is a magnified image of PC3 prostate cancer cells captured using a segregation apparatus described herein. In the image, cells can be seen on or upstream (bulk fluid flow is from left to right in the Figure) from the first segregation step 11 and the second segregation step 12, while few or no cells are present on focusing steps 10.
Figure 10B:
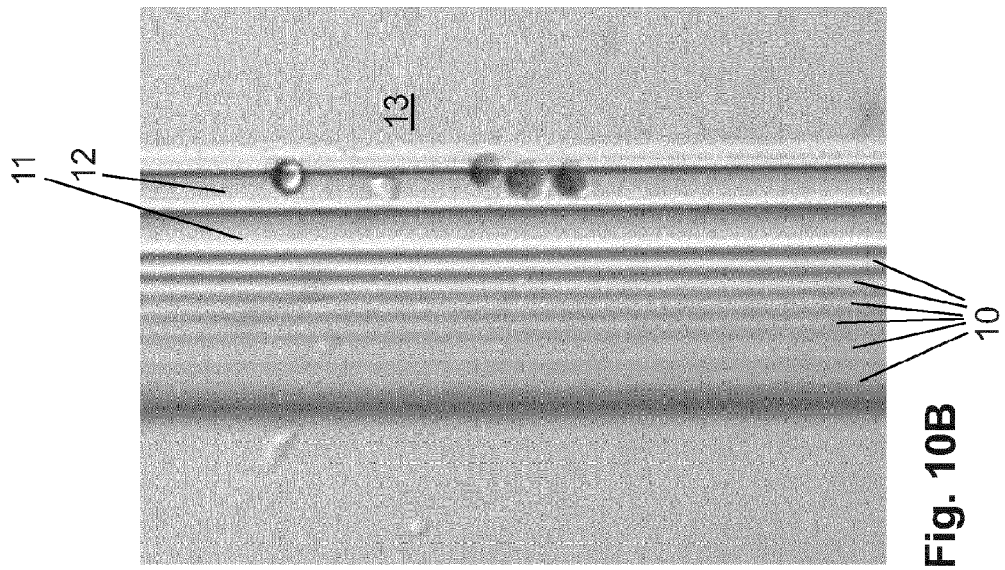
FIG. 10 consists of FIGS. 10A and 10B. Each of these is a magnified image of PC3 prostate cancer cells captured using a segregation apparatus described herein. In each image, cells can be seen on or upstream (bulk fluid flow is from left to right in the Figure) from the first segregation step 11, the second segregation step 12, and the third segregation step 13, while few or no cells are present on focusing steps 10.
Figure 10A:
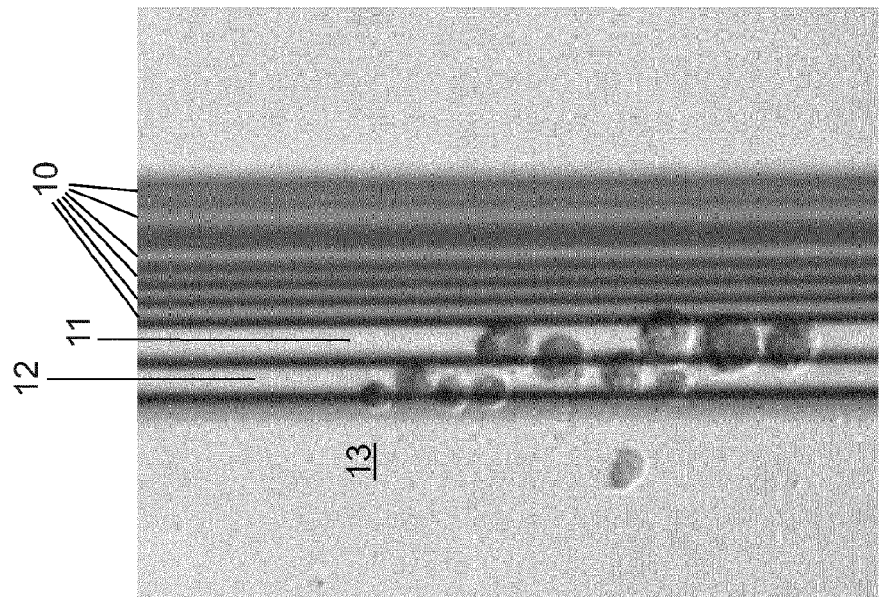

The stepped passageway 55 is the orifice through which particles move, fluid flows, or both, from the inlet region 52 to the outlet region 58 during operation of the apparatus. The separation element 1 has a stepped structure, which defines the stepped shape of at least one side of the stepped passageway 55. The separation element 1 has at one segregating step 11, and it can have multiple segregating steps (e.g., 11-13 in FIGS. 6-8). Fluid must flow through the segregating passageway 101 defined in part by the corresponding segregating step 11 in order to traverse the stepped passageway 55 from the inlet region 52 to the outlet region 58 when the apparatus is assembled.

During operation of the apparatus described herein, a mixture of particles having different sizes can be caused to flow through the stepped passageway 55, including at least one segregating passageway 101. Passage of particles having a characteristic size in excess of the narrow dimension (i.e., the height) of the segregating passageway 101 is impeded at or near the leading edge 31 of the segregating step 11 that bounds the segregating passageway, and such particles will tend to accumulate at or near the leading edge 31 rather than passing through the segregating passageway 101. So long as the segregating passageway 101 is not completely occluded by impeded particles across the entire breadth of the segregating step 11, flow of fluid and particles around or past the impeded cells can continue. Development of the subject matter described herein arose, at least in part, as a result of attempts to design apparatus less susceptible to fouling and clogging by impeded particles than prior art apparatuses. Preferably, the breadth of separating step 11 leading edges 31 are selected so that, for an anticipated mixture of particles, that the portion(s) of the segregating passageway 101 at which passage of particles are impeded has a sufficient flow area that fluid flux through such portion(s) is not significantly (i.e., not more than 50%, 20%, 10%, 5%, 1%, 0.33%, or 0.1% or less) impeded when a desirable or foreseeable number of particles are lodged at the portion(s).

The separation element 1 can include a focusing step 10 (as illustrated in FIGS. 1-6), which serves to deflect fluid flow within the stepped passageway 55 toward the first segregating passageway 101, to fill 'dead spaces' upstream of the first segregating step 11, to provide a structurally sound foundation for carrying segregating steps on the separation element, or some combination of these. The separation need not include a focusing step.

The steps of the separation element 1 can have any of a variety of shapes. In one embodiment (e.g., in the apparatus depicted in FIG. 1), both the focusing step 10 and the first segregating step 11 have a common 'staircase-type' step structure, i.e., two planar surfaces that intersect at a right angle. That is, the transitional face 20 of the focusing step 10 and the broad face 40 of the focusing step 10 meet at a right angle, as do the transitional face 21 of the first segregating step 11 and the broad face 41 thereof. Alternatively, the transitional and broad faces of steps can meet at an angle between 90 and 180 degrees, for example. The transitional and broad faces of the steps can also meet at an angle between 0 and 90 degrees, forming an overhang. For the apparatus described herein, at least one segregating step 11 has a curved or, preferably, invaginated leading edge 31 and transitional face 21, so that the breadth of the step is significantly greater than the width of the step.

Steps having transitional and broad faces that meet at an angle between 90 and 180 degrees can occlude passage of particles having a variety of sizes (i.e., those having sizes intermediate between the narrow dimension of the passageway defined by the broad face of the step and the narrow dimension of the space upstream from the step. By halting passage of particles having slightly different sizes at different positions on the transitional face of the step, a step having transitional and broad faces that meet at an angle between 90 and 180 degrees can prevent clogging of the passageway defined by the broad face of the step to a greater degree than a step having transitional and broad faces that meet at an angle of 90 degrees or less.

Clogging of fluid flow past a step by particles that occlude the passageway defined by the broad face of the step can also be reduced or avoided by increasing the width of the step, as was recognized in the art. Because each particle occludes fluid flow only for the flow area obscured by the particle, a wider step will necessarily be clogged by a greater number of occluding particles. However, increasing the width of a step is not always practical, especially when significant widening is required to accommodate numerous particles or when miniaturization is desired.

A significant aspect of the subject matter disclosed herein is recognition by the present inventors that the capacity of a segregating step 11 to accommodate impeded particles can be significantly increased without increasing the width of the step. Rather than (or in addition to) increasing the width of the segregating step 11, its particle-retention capacity can be increased by increasing the breadth of the leading edge 31 of the step (i.e., where particles impedance occurs), for example by decreasing the straightness of the step.

By way of example, in a fluid channel having a rectangular cross-section, a step that extends directly across (i.e., at right angles to the sides) of the channel has a leading edge with a breadth simply equal to the width of the channel (see, e.g., FIG. 1). If the shape of the step is a hemicircle, with the arc of the hemicircle extending such that the center of the hemicircle lies downstream from the upstream-most edge of the hemicircle, then the breadth of the leading edge of the step is equal to the perimeter of the hemicircle, which is the number pi multiplied by the width of the channel and divided by two (i.e., roughly 1.57× the width of the channel). Similarly, steps having leading edges shaped like an arc of a circle or ellipse, like chevrons (i.e., like the letter V), like zig-zags, like serpentine lines, or like irregular lines (See FIGS. 2-6) will all have breadth values greater than the breadth of a step that simply extends perpendicularly across a fluid channel having a rectangular cross-section. Steps having leading edges with such shapes can be used in the apparatus described herein.

In one embodiment, the leading edge 31 of a segregating step 11 is shaped such that the breadth of the leading edge 31 is substantially greater (e.g., 1.5, 2, 3, 4, 5, 10, 20, 50, 100, or 1000 times greater) than the overall width of the step and/or the width of the segregation passageway 101 defined by the step. This can be achieved, for example, by forming the step such that its leading edge has an undulating or highly irregular edge shape, as illustrated in FIGS. 2 and 3, which are representations of steps having undulating and irregular edges, respectively. In FIG. 2, the segregation step 11 is a flat slab having finger-shaped projections at its transition face 21. The breadth of the leading edge 31 of the step formed by the perimeter of the finger-shaped projections is substantially greater than the width of the step, as can be seen clearly in FIG. 2A. Likewise, the undulations and irregularities in the leading edge of the segregation step 11 illustrated in FIG. 3 cause the breadth of the leading edge to be substantially greater than the overall width of the step, as can be seen clearly in FIG. 3A.

Multiple steps can have similarly- or differently-shaped leading edges. FIGS. 4-6, for example, illustrate separation elements 1 in which a focusing step 10 (which does not necessarily impede passage of any particles is shaped differently from each of segregating steps 11-13. In these illustration segregating steps 11-13 have the same or similar shapes, but they need not. Regardless of the shape of the leading edge 31 of a segregating step 11, what is important to passage of cells or other particles through the segregating passageway 101 bounded by the steps is the narrow dimension (height; e.g., $h_1$ in FIG. 1D) defined by each segregating step 11. Particles unable to pass through the narrow dimension defined by a segregating step 11 will not traverse the step (unless it is able to deform and the pressure drop across the step is sufficient to induce such deformation).

A series of segregating steps having progressively narrowing passageways defined thereby, a segregating step having an inclined broad face (i.e., so that the narrow passageway defined thereby narrows in the direction of bulk fluid flow therethrough), or a combination of these can be used to capture deformable cells (i.e., cells which can deform to fit within, but not pass through, the passageway defined by a segregating step) and to segregate them from cells that are either sufficiently small or sufficiently deformable to pass the segregating step(s).

The breadth of each segregating step 11 can be selected based on the anticipated accumulation of particles on the step, in view of the particle composition of sample anticipated to be processed using the apparatus and the narrow dimension of each corresponding segregating passageway 101. The breadth of a segregating step 11 can be selected to be significantly (e.g., 10, 1,000, or 100,000 times) greater than the narrow dimension of the corresponding segregating passageway 101. By way of example, for segregation of fetal-like cells from maternal blood, a breadth approximately at least 1,000 (one thousand), and preferably 10,000 (ten thousand), times the narrow dimension of the corresponding passageway is considered desirable. Segregating steps 11 having relatively large breadth permit accumulation of particles within a segregating passageway 101 while limiting clogging of the segregating passageway 101.

Although the apparatus has been described herein with reference to a single segregating step 11 (FIGS. 1-3 and 7) and with reference to three segregating steps 11 (FIGS. 4-6), substantially any number of segregating steps 11 (e.g., two, four, ten, or one hundred steps) can be included in the apparatus, each segregating step 11 defining a corresponding segregating passageway 101 within the stepped passageway 55 and having a characteristic narrow dimension.

Materials and Methods of Construction

The materials and methods used to make the devices described herein can be substantially the same as those described previously in U.S. Pat. No. 7,993,908, in PCT publication WO 2011/066497, or elsewhere, so long as the leading edge 31 of at least one segregating step 11 of the apparatus can be constructed as described herein—e.g., having a breadth significantly greater than its width, such as a leading edge 31 having an undulating shape. That is, the methods must be able to make a device having at least one segregating step 11 having a leading edge 31 breadth greater than the overall width of the step (e.g., greater than the width of a passageway within the device in which the step occurs).

Segregable Particles

The devices described herein can be used to segregate substantially the same kinds of particles as those described previously in U.S. Pat. No. 7,993,908, in PCT publication WO 2011/066497. Attributes of the particles that affect their ability to traverse the segregation passageway(s) 101 of the apparatus described herein include the size, shape, surface properties, and deformability of the particles.

In an important embodiment, the apparatus is used to segregate tumor cells (which tend to be significantly larger than corresponding non-tumor cells of the same cell type) from non-tumor cells. It is known that tumor cells circulate in the bloodstream of many individual humans (as well as other vertebrate animals), even for tumors that are considered solid, unitary tumors, such as ovarian, prostate, and breast cancers. Detection and/or enumeration of circulating tumor cells (CTCs) can be an important indicator of the presence, nature (e.g., stage or grade), malignancy, and response to treatment of a tumor. Furthermore, isolation of CTCs permits identification of the type of tumor that is present. These characteristics can be significantly important for diagnosis, treatment, and prevention of metastasis of tumors.

In one embodiment, blood obtained from an individual (e.g., human) subject is processed using an apparatus described herein to segregate CTCs from the blood. Segregated CTCs can be recovered and analyzed by any known method to obtain important diagnostic, therapeutic, and preventative information specific to the individual subject. Because CTCs are believed to be present even before development or establishment of many advanced tumors, detection and characterization of CTCs can enable early, effective intervention to prevent tumor development and spread.

Substantially any diagnostic procedure amenable to use of isolated cells can be performed using cells that are obtained from the device described herein. Examples of such methods include assessing the affinity of an antibody preparation with such cells or an extract prepared from them, assessing nucleic acids contained within such cells, or assessing the ability of the cells to grow in the presence of a selected medium or to interact with other cells. Cells obtained using the devices described herein can thus be used to assess gene expression, genetic changes, biomarker display, or other morphological or biochemical features of the cells (or changes to such features).

In another embodiment, the apparatus described herein is used to segregate circulating endothelial cells (CECs) from a sample including such cells, such a blood sample taken from a patient. CECs having an enlarged size (relative to normal CECs) can also be segregated by selecting appropriate narrow passageway dimensions in the apparatus. By way of example, an apparatus can be used which has narrow passageway dimensions selected to segregate enlarged CECs from normal CECs. Further by way of example, an apparatus can be used which has narrow passageway dimensions selected to segregate all CEC (or only enlarged CECs) from the cells normally present in blood. CECs are known to be indicative of the presence or occurrence of trauma in an individual, and the presence of enlarged CECs can be particularly indicative of certain conditions, such as acute or impending myocardial infarction (see, e.g., Damani et al., 2012, Sci. Transl. Med. 4:126ra33). CECs isolated using the apparatus described herein can also be recovered as described herein and/or analyzed by conventional methods (e.g., by detection of immunological cell-surface markers) to identify their tissue of origin and thereby further indicating the type and/or body location of the trauma that induced their circulation. By way of example, isolation of enlarged CECs of cardiac origin is indicative that the patient has recently undergone, is currently undergoing, or is imminently at risk for occurrence of a myocardial infarction.

Fluid Displacement Devices

The apparatus described herein can be operated using substantially the same types of fluid displacement devices as those described previously in U.S. Pat. No. 7,993,908, in PCT publication WO 2011/066497, or in the literature pertaining to other microfluidic devices.

Using the Apparatus

Use and operation of the apparatus described herein are substantially the same as described previously in documents incorporated herein by reference. The apparatus described herein have the significant advantage of exhibiting less susceptibility to clogging, flow/throughput impairment, and other undesirable phenomena attributable to capture of cells on a segregating step 11 thereof.

EXAMPLES

The subject matter of this disclosure is now described with reference to the following Examples. These Examples are provided for the purpose of illustration only, and the subject matter is not limited to these Examples, but rather encompasses all variations which are evident as a result of the teaching provided herein.

In one embodiment, the stepped passageway has an overall width of 2.5 centimeters and includes a second step 62 having an undulating leading edge having a breadth of 8.0 centimeters. The narrow dimension of the second passageway 52 between the second step 62 and the opposed cover 4 is 10 micrometers.

When a suspension of cells (e.g., 10 milliliters of human blood having a selected number of tumor cells included therein) is passed through the stepped passageway, followed by a rinsing solution that does not lyse the tumor cells, substantially all blood cells pass through the apparatus and most or all of the tumor cells are retained within it.

TABLE 1

| Parts List | |
|---|---|
| 1 | Separation Element |
| 2 | Body |
| 4 | Cover |
| 10 | Focusing Step |
| 11 | (First) Segregating Step |
| 12 | Second Segregating Step |
| 32 | Leading Edge of Second Segregating Step |
| 13 | Third Segregating Step |
| 20 | Transitional Face of Focusing Step |
| 21 | Transitional Face of (First) Segregating Step |
| 22 | Transitional Face of Second Segregating Step |
| 23 | Transitional Face of Third Segregating Step |
| 30 | Leading Edge of Focusing Step |
| 31 | Leading Edge of (First) Segregating Step |
| 32 | Leading Edge of Second Segregating Step |
| 33 | Leading Edge of Third Segregating Step |
| 40 | Broad Face of Focusing Step |
| 41 | Broad Face of (First) Segregating Step |
| 42 | Broad Face of Second Segregating Step |
| 43 | Broad Face of Third Segregating Step |
| 50 | Void defined by body and cover |
| 52 | Inlet Region of Void |
| 53 | Upstream Portion of channel |
| 54 | Channel connecting inlet and outlet regions of void |
| 55 | Separating Portion of channel |
| 56 | Downstream Portion of channel |
| 58 | Outlet Region of Void |

TABLE 1-continued

| Parts List | |
|---|---|
| 60 | Part of Separating Portion bounded by Focusing step |
| 61 | Part of Separating Portion bounded by (First) Segregating Step |
| 62 | Part of Separating Portion bounded by Second Segregating Step |
| 63 | Part of Separating Portion bounded by Third Segregating Step |
| 101 | (First) Segregating Passageway |
| 102 | Second Segregating Passageway |
| 103 | Third Segregating Passageway |

TABLE 2

| Abbreviations List | |
|---|---|
| BFF | Bulk Fluid Flow |
| hc | Height of Channel |
| h0 | Height of Channel in portion bounded by Focusing Step |
| h1 | Height of Channel in portion bounded by (First) Segregating Step |
| h2 | Height of Channel in portion bounded by Second Segregating Step |
| h3 | Height of Channel in portion bounded by Third Segregating Step |
| W | Overall Width of Channel in the Separating Portion |
| L | Length of Separating Portion |
| B | Breadth of Leading Edge of a Segregating Step |
| D | ratio B/L |
| W | Width of a Segregating Step |

The disclosure of every patent, patent application, and publication cited herein is hereby incorporated herein by reference in its entirety.

While the subject matter has been disclosed herein with reference to specific embodiments, it is apparent that other embodiments and variations of this subject matter can be devised by others skilled in the art without departing from the true spirit and scope of the subject matter. The appended claims include all such embodiments and equivalent variations.

What is claimed is:

1. A method of segregating circulating endothelial cells (CECs) from blood cells in a fluid sample, wherein said method employs a device comprising:
    a body and
    a cover that define a void therebetween, the void containing
        a separation element that segregates an inlet region and an outlet region of the void, the separation element defining, together with a surface of the void,
        a channel that fluidly connects the inlet and outlet regions by way of a separating portion into which the separation element projects, the channel having
        an overall width at the separating portion and
        a height defined by the distance between the separation element and the surface of the void,
    at least one of the body, the cover or the separation element bearing a segregating step disposed within and having a leading edge extending substantially completely across the separating portion of the channel, whereby the channel is divided into an upstream portion on the inlet side of the leading edge and a substantially lamellar downstream portion on the outlet side of the leading edge, the upstream portion of the channel being also lamellar in a region between the inlet region and the separation element;
    the height of the upstream portion being sufficient to facilitate passage therethrough of both said CECs and said blood cells, the height of the downstream portion being sufficiently large to facilitate passage therethrough of said blood cells and sufficiently small to inhibit passage therethrough of said CECs, and the leading edge having a length greater than the overall width of the channel at the separating portion;

and said method comprises urging said fluid sample through said channel of said device from the inlet region whereby CECs will be segregated from said blood cells due to their characteristics and inability to traverse said segregating step along the separating portion of the channel.

2. The method as claimed in claim 1 which further comprises recovering said segregated CECs that are unable to pass to the outlet region.

3. The method as claimed in claim 2 which further comprises backflushing fluid from the outlet region in the direction of the inlet region to recover said segregated CECs.

4. The method as claimed in claim 1 wherein said device has a size approximately equal to a microscope slide.

5. The method as claimed in claim 1 wherein said leading edge has an undulating or invaginated shape.

6. The method as claimed in claim 5 wherein said leading edge has a serpentine shape.

7. The method as claimed in claim 1 wherein the separation element of said device includes a plurality of segregating steps disposed serially within the separating portion, each segregating step:
   (a) having a leading edge that extends substantially across the separating portion and having a length substantially greater than the overall width of the channel at the separating portion; and
   (b) dividing the channel into an upstream portion and a substantially lamellar downstream portion relative to the leading edge of the segregating step, the height of the channel at the downstream portion immediately following the segregating step being smaller than the height of the channel at the upstream portion immediately preceding the segregating step.

8. The method of claim 1 wherein said sample is a whole blood sample.

9. The method of claim 8 wherein said CECs are enlarged CECs of cardiac origin.

10. The method as claimed in claim 1 wherein said CECs are enlarged CECs of cardiac origin.

11. A method of determining an indication of trauma associated with occurrence of circulating endothelial cells (CECs) in an individual, the method comprising the steps of:
   (i) segregating CECs from the whole blood sample obtained from the individual using a method according to claim 8 and
   (ii) determining the occurrence of thus segregated CECs, wherein said occurrence of segregated CECs is indicative of occurrence of a trauma in the individual.

12. A method of determining an indication that an individual has a status selected from the group consisting of (a) has recently undergone, (b) is currently undergoing, or (c) is imminently at risk of occurrence of myocardial infarction, the method comprising the steps of:
   (i) segregating enlarged CECs of cardiac origin from the whole blood sample obtained from the individual using a method according to claim 9 and
   (ii) determining the occurrence of thus segregated enlarged CECs of cardiac origin, wherein said occurrence of segregated enlarged CECs of cardiac origin is indicative of a status (a), (b) or (c) as above in the individual.

* * * * *